United States Patent [19]

Ozawa et al.

[11] Patent Number: 5,319,132
[45] Date of Patent: Jun. 7, 1994

[54] PROCESS FOR PRODUCING HALOMETHYL ESTER OF ALIPHATIC CARBOXYLIC ACID

[75] Inventors: Noriyuki Ozawa; Naoto Yazawa, both of Shizuoka, Japan

[73] Assignee: Ihara Chemical Industry Co., Ltd., Tokyo, Japan

[21] Appl. No.: 74,813

[22] PCT Filed: Oct. 16, 1992

[86] PCT No.: PCT/JP92/01350
§ 371 Date: Jun. 15, 1993
§ 102(e) Date: Jun. 15, 1993

[87] PCT Pub. No.: WO93/08152
PCT Pub. Date: Apr. 29, 1993

[30] Foreign Application Priority Data

Oct. 18, 1991 [JP] Japan .................. 3-297913

[51] Int. Cl.$^5$ .................. C07C 69/63; C07C 67/10
[52] U.S. Cl. .................. 560/236
[58] Field of Search .................. 560/236, 62; 435/130

[56] References Cited

U.S. PATENT DOCUMENTS 4,182,902  1/1980  Thiele et al. .................. 560/62 X
5,240,836  8/1993  Harper .................. 435/130

FOREIGN PATENT DOCUMENTS 63-152341  6/1988  Japan .
3-41052    2/1991  Japan .
3-188044   8/1991  Japan .
4-5259     1/1992  Japan .

*Primary Examiner*—Arthur C. Prescott
*Attorney, Agent, or Firm*—Oblon, Spivak, McClelland, Maier & Neustadt

[57] ABSTRACT

The present invention provides a process for producing a halomethyl ester of an aliphatic carboxylic acid in which a metal salt of an aliphatic carboxylic acid is reacted with a dihalomethane in the presence of a phase transfer catalyst, whereby the efficient production of a halomethyl ester of an aliphatic carboxylic acid has been made possible without the formation of a halomethyl ether as a by-product. The bis compound bis[aliphatic carbonyloxy)methane], which is obtained as a by-product, is hydrolyzed to enable the quantitative recovery of an aliphatic carboxylic acid and its reuse. Thus, the present process is preferable as a process for industrial production of a halomethyl ester of an aliphatic carboxylic acid.

2 Claims, No Drawings

PROCESS FOR PRODUCING HALOMETHYL ESTER OF ALIPHATIC CARBOXYLIC ACID

TECHNICAL FIELD

The present invention relates to a process for producing a halomethyl ester of an aliphatic carboxylic acid safely and economically in industry.

Halomethyl esters of aliphatic carboxylic acids are useful as raw materials for medicines, agricultural chemicals, etc., for example, as raw materials for oral beta lactam antibiotics such as Pivampicillin, Pivmecillinam, Seftelam, Pivoxyl and the like.

BACKGROUND ART

For production of a halomethyl ester of an aliphatic carboxylic acid, there have hitherto been known processes by so-called chloromethylation (Blanc-Quelet reaction), such as a process described in J. Am. Chem. Soc., 89, 21, 5439 (1967) wherein pivaloyl chloride is reacted with formaldehyde in the presence of zinc chloride, and a process described in Otkrytiya, Izobret., 20, 102 (1987) wherein pivalic acid is reacted with thionyl chloride and paraformaldehyde in the presence of zinc chloride. These processes, however, have had a problem that chloromethyl methyl ether and bis(chloromethyl) ether (these highly toxic ethers are hereinafter referred to as halomethyl ether) are formed as by-products.

Further, in Japanese Patent Application Kokai (Laid-open) No. 152341/1988 is proposed a process wherein an alkali metal salt of an aliphatic carboxylic acid is reacted with a dihalohydrocarbon in a solvent such as alcohol, aliphatic nitrile, ether or the like. It is described in the document that even a dihalomethane can be used as the dihalohydrocarbon. However, our confirmation test for the process revealed that relatively good results were obtained when the dihalohydrocarbon had two or more carbon atoms but, in the reaction with a dihalomethane, only a bis(aliphatic carboxy)methane (a by-product) was formed and substantially no halomethyl ester of an aliphatic carboxylic acid intended by the process was obtained. A similar process is described in Japanese Patent Application Kokai (Laid-open) No. 188044/1991. In this process also, a bis(aliphatic carboxy)methane is formed as a main product.

Furthermore, in Japanese Patent Application Kokai (Laid-open) No. 41052/1991 is proposed a process wherein a metal salt of an alkanoic acid is reacted with a large excess amount of a dihaloalkane in the presence of dimethylformamide or the like at a low temperature for a long period of time (at least 30 hours) to produce a haloalkyl ester of an alkanoic acid. In this process, however, a long reaction time (at least 30 hours) is required; since a dialkylamide of an alkanoic acid such as dimethylformamide or the like is used as a third component, a step for separation and recovery thereof is required; and a yield of an intended product is as low as 16–59%. Thus, the process has not been satisfactory as an industrial process.

The present invention has been made with the aim of providing a process for producing a halomethyl ester of an aliphatic carboxylic acid, which forms no halomethyl ether as by-product (this is highly toxic and highly carcinogenic) and which is advantageous in industrial application.

DISCLOSURE OF THE INVENTION

The present inventors conducted a research on a process for producing a halomethyl ester of an aliphatic carboxylic acid, which forms no halomethyl ether and which is advantageous in industrial application. As a result, the present inventors found that the object can be achieved by using, in particular, a phase transfer catalyst in the reaction of a metal salt of an aliphatic carboxylic acid with a dihalomethane. The finding has led to the completion of the present invention.

The present invention provides a process for producing a halomethyl ester of an aliphatic carboxylic acid, which is characterized by reacting a metal salt of an aliphatic carboxylic acid with a dihalomethane in the presence of a phase transfer catalyst.

BEST MODE FOR CARRYING OUT THE INVENTION

The present invention is described in detail below.

In the present invention, as the metal salt of an aliphatic carboxylic acid used as a raw material, there are used, for example, alkali metal or alkaline earth metal salts of C1-10 straight-chain, branched-chain or cyclic aliphatic carboxylic acids. As the aliphatic carboxylic acids, there can be mentioned, for example, formic acid, acetic acid, propionic acid, n-butyric acid, isobutyric acid, pivalic acid, cyclohexanecarboxylic acid, cyclopentaneacetic acid, caprylic acid, nnonanoic acid and octanoic acid. As the metal salts, there can be used, for example, sodium salts, potassium salts, magnesium salts, calcium salts and barium salts of aliphatic carboxylic acids. These metal salts of aliphatic carboxylic acids can be easily produced by reacting an aliphatic carboxylic acid with a hydroxide, carbonate or hydrogencarbonate of an alkali metal or alkaline earth metal. Each of the resulting salts of aliphatic carboxylic acids may be used as it is, without being isolated.

As the dihalomethane, there can be used dihalomethanes obtained by subjecting methane to substitution with halogen atoms of chlorine, bromine, iodine, etc. The two halogen atoms in dihalomethane are preferably different from each other. Of the dihalomethanes, preferable are bromochloromethane, chloroiodomethane, bromoiodomethane, etc. The dihalomethane is used in an amount of 1–100 moles, preferably 3–50 moles per mole of the metal salt of an aliphatic carboxylic acid, and the excess amount of the dihalomethane can be easily recovered after the reaction and reused.

In the process of the present invention, the presence of a phase transfer catalyst is necessary in the reaction of a metal salt of an aliphatic carboxylic acid with a dihalomethane. As the phase transfer catalyst, there may be used any substance ordinarily called "phase transfer catalyst". However, there are generally used quaternary onium salts such as quaternary ammonium salt, quaternary pyridinium salt, quaternary phosphonium salt and the like; inclusion compounds such as crown ether, cryptand, polyethylene glycol and the like; and so forth. Further, there may be used tertiary amines which react with the dihalomethane in the reaction system to form a quaternary onium salt. Also, there may be used at least one substance freely selected from those mentioned above. Specific examples of the phase transfer catalyst include tetrabutylammonium bromide, tetrabutylammonium chloride, tetrabutylammonium hydrogensulfate, tetrabutylammonium hydroxide, tetrabutylammonium tetrafluoroborate, tetrabutylammonium perchlorate, trioctylmethylammonium chloride, trioctylmethylammonium bromide, tetraphenylphosphonium bromide, tetraphenylphosphonium chloride, benzyltriphenylphosphonium chloride, tetrabutylphosphonium bromide, tetrabutylphosphonium chloride, 18-crown-6, dibenzo-18-crown-6, polyethylene glycol, 1-laurylpyridinium chloride, tris(3,6-dioxaheptyl)amine [TDA-1], N,N,N',N'-tetramethylethylenediamine, N,N,N',N'-tetramethylpropanediamine and triethylamine, all of which are easily available commercially.

The preferable amount of the phase transfer catalyst is at least 0.01 mole %, preferably at least 0.05 mole % based on the metal salt of an aliphatic carboxylic acid.

Next, description is made on the specific mode for preferably carrying out the present invention. First, a phase transfer catalyst, a metal salt of an aliphatic carboxylic acid and a dihalomethane are mixed in given proportions and reacted. In this case, there is no particular restriction to the addition order of the metal salt of an aliphatic carboxylic acid (or, an aliphatic carboxylic acid and a corresponding base), the dihalomethane and the phase transfer catalyst.

The reaction temperature has no particular restriction and is generally appropriate to be in the range of 0° C. and the reflux temperature of the reaction system. The reaction time depends upon the kinds of raw materials used, the reaction temperature, the catalyst, etc. but is generally about 15 minutes to 20 hours. The reaction pressure may be normal pressure or applied pressure. When a metal salt of an aliphatic carboxylic acid is formed in the reaction system, water of a corresponding amount is generated in the reaction system; but the presence of this amount of water may cause no problem. This water may be removed out of the reaction system by azeotropic distillation or the like; or may not be removed to conduct the reaction of the present invention. When the water is removed, improvement in selectivity, etc. is expected.

After the completion of the reaction, water is added and the resulting mixture is allowed to stand, whereby an aqueous layer and an organic layer are separated. Only the organic layer is taken, water-washed and subjected to distillation to obtain a desired halomethyl ester of an aliphatic carboxylic acid.

In the present invention, a bis(aliphatic carbonyloxy)methane (hereinafter referred also to as bis compound) is obtained as a by-product from a distillation residue. This bis compound, by being hydrolyzed with an alkali or an acid, can be recovered as an aliphatic carboxylic acid substantially quantitatively for reuse as said acid. Therefore, the aliphatic car boxylic acid used as a raw material is consumed only by the amount used for the formation of its halomethyl ester, which is efficient.

The present invention is hereinafter described specifically by way of Examples and Reference Examples.

EXAMPLE 1

Into a 1,000-ml reaction flask equipped with a reflux condenser, a thermometer and a stirrer were added 646.9 g (5 moles) of bromochloromethane, 32.6 g (0.5 mole) of 86% potassium hydroxide and 51.1 g (0.5 mole) of pivalic acid to form potassium pivalate. In this case, since water was formed in a corresponding amount, it was removed by azeotropy with bromochloromethane. When the water removal was over, 0.2 g of tetraphenylphosphonium bromide was fed and a reaction was conducted for 2.5 hours. The reaction temperature was 64°-65° C.; the conversion was 98.6%; the selectivity of chloromethyl pivalate was 65.4%; and the selectivity of a bis compound was 32.9% [neither chloromethyl methyl ether nor bis(chloromethyl) ether was detected in the reaction mixture]. Incidentally, the conversion, etc. were obtained by acidifying the reaction mixture, subjecting the extract to gas chromatography, and using the resulting chart to make calculation by the total area method.

After the completion of the reaction, water was added to dissolve the inorganic salt formed and the unreacted potassium salt, and the resulting mixture was allowed to stand. The separated organic layer was taken, water-washed and subjected to distillation to obtain 563.9 g (recovery: 95%) of bromochloromethane as a fraction of 67° C. (boiling point). The distillation residue was subjected to vacuum distillation at 50 mmHg to obtain 43.7 g of chloromethyl pivalate as a fraction of 70°-72° C. (boiling point). 17.8 g of the vacuum distillation residue was stirred in 80 g of concentrated hydrochloric acid at 90° C. for 7 hours; the resulting mixture was allowed to stand; the organic layer was separated to obtain 16.0 g of pivalic acid. As a result, the yield of chloromethyl pivalate based on pivalic acid was 84.4%.

Incidentally, the selectivity and the selectivity of bis compound were calculated as follows.

| | |
|---|---|
| Selectivity (%) = | [(yield (%) of desired product)/(conversion (%) of aliphatic carboxylic acid)] × 100 |
| Selectivity of bis compound (%) = | [(yield (%) of bis compound)/(conversion (%) of aliphatic carboxylic acid)] × 100 |

EXAMPLE 2

Into a 200-ml reaction flask equipped with a reflux condenser, a thermometer and a stirrer were added 64.7 g (0.5 mole) of bromochloromethane, 7.0 g (0.05 mole) of potassium pivalate and 0.42 g (2 mole %) of tetraphenylphosphonium bromide. They were reacted at room temperature for 6 hours. [Neither chloromethyl methyl ether nor bis(chloromethyl) ether was detected in the reaction mixture.]

In the reaction, the conversion was 96.7%; the selectivity was 65.8%; and the selectivity of bis compound was 33.3%.

EXAMPLES 3-15

Reactions were conducted in the same manner as in Example 2 except that the catalyst, reaction temperature and reaction time used in Example 2 were changed in each reaction. The reaction conditions, conversions, selectivities, etc. are shown in Table 1.

TABLE 1

| | Catalyst and its amount | Reaction temperature °C. | Reaction time hr | Convession % | Selectivity % | Selectivity of bis compound % |
|---|---|---|---|---|---|---|
| 3 | Tetrabutylammonium bromide 2.0 mole % | Room temp. to 43 | 3.5 | 97.2 | 58.7 | 40.4 |
| 4 | Tetrabutylammonium hydrogensulfat 2.0 mole % | Room temp. to 42 | 8.0 | 85.1 | 58.9 | 40.2 |
| 5 | Tetrabutylammonium tetrafluoroborate 2.0 mole % | Room temp. to 42 | 7.0 | 87.6 | 58.4 | 41.1 |
| 6 | Tetrabutylammonium perchlorate 2.0 mole % | Room temp. to 42 | 9.0 | 87.9 | 56.2 | 43.1 |
| 7 | Triooctylmethylammonium chloride 2.0 mole % | Room temp. to reflux temp. | 8.0 | 86.2 | 54.5 | 44.2 |
| 8 | Tetrabutylphosphonium bromide 2.0 mole % | Room temp. | 9.0 | 88.8 | 59.9 | 39.3 |
| 9 | 18-Crown-6 2.0 mole % | Room temp. to reflux temp. | 9.0 | 98.1 | 49.1 | 47.4 |
| 10 | Dibenzo-18-crowm-6 2.0 mole % | Room temp. to reflux temp. | 11.0 | 92.9 | 52.9 | 45.4 |
| 11 | Polyethylene glycol #400 2.0 mole % | Room temp. to reflux temp. | 8.0 | 87.6 | 53.4 | 45.8 |
| 12 | NNN'N'-tetramethylethylenediamine 2.0 mole % | Room temp. to reflux temp. | 11.5 | 88.8 | 35.7 | 62.3 |
| 13 | Triethylamine 2.0 mole % | Room temp. to 35 | 7.0 | 96.6 | 46.7 | 52.3 |
| 14 | Tris(3,6-dioxaheptyl)amine 2.0 mole % | Room temp. to 35 | 10.5 | 93.7 | 54.1 | 44.8 |
| 15 | 1-Laurylpyridinium chloride 2.0 mole % | Room temp. to 40 | 9.0 | 84.7 | 51.3 | 47.6 |

EXAMPLES 16-20

Reactions were conducted in the same manner as in Example 2 except that the catalyst amount and the amount of bromochloromethane used in Example 2 were changed in each reaction. The reaction conditions, conversions, selectivities, etc. are shown in Table 2.

TABLE 2

| | Catalyst and its amount | Bromochloromethane amount Equivalent | Reaction temperature °C. | Reaction time hr | Convession % | Selectivity % | Selectivity of bis compound % |
|---|---|---|---|---|---|---|---|
| 16 | Tetraphenylphosphoniun bromide 0.25 mole % | 10.0 | Reflux temp. | 2.5 | 99.1 | 65.2 | 31.6 |
| 17 | Tetraphenylphosphoniun bromide 0.05 mole % | 10.0 | Reflux temp. | 8.0 | 88.8 | 72.7 | 26.6 |
| 18 | Tetraphenylphosphoniun bromide 2 mole % | 5.0 | Room temp. | 7.0 | 86.4 | 50.0 | 49.1 |
| 19 | Tetraphenylphosphoniun bromide 2 mole % | 10.0 | Room temp. | 7.0 | 91.7 | 65.5 | 33.5 |
| 20 | Tetraphenylphosphoniun bromide 2 mole % | 20.0 | Room temp. to 44 | 9.0 | 99.0 | 72.2 | 25.6 |

EXAMPLE 21

Into a 200-ml reaction flask equipped with a reflux condenser, a thermometer and a stirrer were added 64.7 g (0.5 mole) of bromochloromethane, 3.26 g (0.05 mole) of 86% potassium hydroxide, 0.32 g (2 mole %) of tetrabutylammonium bromide and 5.1 g (0.05 mole) of pivalic acid. They were reacted for 8 hours. [Neither chloromethyl methyl ether nor bis(chloromethyl) ether was detected in the reaction mixture.]

Incidentally, the reaction temperature was 40° C. to the reflux temperature. In the reaction, the conversion was 91.9%; the selectivity was 49.7%; and the selectivity of bis compound was 49.1%.

EXAMPLE 22

Into a 1,000-ml reaction flask equipped with a reflux condenser, a thermometer and a stirrer were added 646.9 g (5 mole) of bromochloromethane, 32.6 g (0.5 mole) of 86% potassium hydroxide, 0.32 g (0.2 mole %) of tetraphenylphosphonium bromide and 51.0 g (0.5 mole) of potassium pivalate. They were reacted at the reflux temperature for 6 hours. [Neither chloromethyl methyl ether nor bis(chloromethyl) ether was detected in the reaction mixture.]

Incidentally, the reaction temperature was the reflux temperature. In the reaction, the conversion was 96.7%; the selectivity was 61.0%; and the selectivity of bis compound was 37.4%.

EXAMPLES 23-26

Reactions were conducted in the same manner as in Example 2 except that the reaction temperature, reaction time and potassium salt of aliphatic carboxylic acid used in Example 2 were changed in each reaction. The reaction conditions, conversions, selectivities, etc. are shown in Table 3.

TABLE 3

| | Aliphatic carboxylic acid | Reaction temperature °C. | Reaction time hr | Convession % | Selectivity % | Selectivity of bis compound % |
|---|---|---|---|---|---|---|
| 23 | Isobutyric acid | Room temp. | 8.0 | 94.3 | 57.0 | 41.9 |
| 24 | Caprylic acid | Room temp. to 50 | 6.0 | 93.3 | 40.8 | 55.9 |
| 25 | n-Nonanoic acid | Room temp. to reflux temp. | 7.0 | 99.0 | 31.9 | 51.5 |
| 26 | Acetic acid | 40 to 50 | 3.5 | 98.3 | 48.8 | 45.5 |

EXAMPLE 27

Into a reaction flask equipped with a reflux condenser, a thermometer and a stirrer were added 129.9 of bromochloromethane, 6.21 g of sodium pivalate and 0.264 g of 18-crown-6 as a phase transfer catalyst. They were reacted for 8 hours. [Neither chloromethyl methyl ether nor bis(chloromethyl) ether was detected in the reaction mixture.]

Incidentally, the reaction temperature was room temperature to 49° C. In the reaction, the selectivity was 60.4% and the selectivity of bis compound was 36.3%.

COMPARATIVE EXAMPLE 1

12.9 g (0.1 mole) of bromochloromethane, 15.4 g (0.11 mole) of potassium pivalate and 41.0 g of acetonitrile (a solvent) were added into a 200-ml reaction flask equipped with a reflux condenser, a thermometer and a stirrer and reacted for 14 hours, in accordance with the process described in Japanese Patent Application Kokai (Laid-open) No. 152341/1988.

The reaction temperature was room temperature to the reflux temperature. In the reaction, the conversion was 94.2%; the selectivity was 2.0%; and the selectivity of bis compound was 97.3%. Thus, most of the reaction products was a bis compound.

COMPARATIVE EXAMPLE 2

6.5 g (0.05 mole) of bromochloromethane, 5.4 g (0.055 mole) of potassium acetate, 13 ml of ethyl acetate (a solvent) and 0.08 g (0.25 mM) of tetrabutylammonium bromide (a phase transfer catalyst) were added into a 200-ml reaction flask equipped with a reflux condenser, a thermometer and a stirrer and reacted for 20 hours, in accordance with the process described in Japanese Patent Application Kokai (Laid-open) No. 188044/1991.

The reaction temperature was 50° C. to the reflux temperature. In the reaction, the conversion was 80.2%; the selectivity was 3.39%; and the selectivity of bis compound was 96.1%.

COMPARATIVE EXAMPLE 3

6.5 g (0.05 mole) of bromochloromethane, 7.7 g (0.055 mole) of potassium pivalate, 13 ml of isobutyl acetate (a solvent) and 0.08 g (0.25 mM) of tetrabutylammonium bromide (a phase transfer catalyst) were added into a 200-ml reaction flask equipped with a reflux condenser, a thermometer and a stirrer and reacted for 20 hours, in accordance with the process described in Japanese Patent Application Kokai (Laid-open) No. 188044/1991.

The reaction temperature was 50° C. to 85° C. In the reaction, the conversion was 93.4%; the selectivity was 1.57%; and the selectivity of bis compound was 96.7%.

INDUSTRIAL APPLICABILITY

In the present invention, a metal salt of an aliphatic carboxylic acid is reacted with a dihalomethane in the presence of a phase transfer catalyst; no halomethyl ether is formed as a by-product; and a halomethyl ester of an aliphatic carboxylic acid can be produced at a high yield. The bis compound [bis(aliphatic carbonyloxy)methane], which is obtained as a byproduct, is hydrolyzed to enable the quantitative recovery of an aliphatic carboxylic acid and its reuse. Thus, the present invention is preferable as a process for industrial production of a halomethyl ester of an aliphatic carboxylic acid.

We claim:

1. A process for producing a halomethyl ester of an aliphatic carboxylic acid, which is characterized by reacting a metal salt of an aliphatic carboxylic acid with a dihalomethane in the presence of a phase transfer catalyst.

2. A process for producing a halomethyl ester of an aliphatic carboxylic acid according to claim 1, wherein the dihalomethane is used in an amount of 3–50 moles per mole of the aliphatic carboxylic acid.

* * * * *